(12) United States Patent
Koufman et al.

(10) Patent No.: US 8,729,050 B2
(45) Date of Patent: May 20, 2014

(54) METHOD FOR PREVENTION AND TREATMENT OF REFLUX INJURY IN THE AERODIGESTIVE TRACT AND LARYNGOPHARYNX CAUSED BY PEPSIN

(75) Inventors: Jamie Koufman, New York, NY (US); Michael James, Ramsey (GB); Peter Josling, Battle (GB)

(73) Assignee: Euphora Ltd. (GB)

( * ) Notice: Subject to any disclaimer, the term of this patent is extended or adjusted under 35 U.S.C. 154(b) by 0 days.

(21) Appl. No.: 12/575,366

(22) Filed: Oct. 7, 2009

(65) Prior Publication Data

US 2010/0021554 A1    Jan. 28, 2010

Related U.S. Application Data

(63) Continuation of application No. 11/953,029, filed on Dec. 8, 2007, now abandoned.

(51) Int. Cl.
*A61K 31/717* (2006.01)
*A61K 31/715* (2006.01)
*A61K 9/14* (2006.01)

(52) U.S. Cl.
USPC .................. 514/57; 514/54; 536/56; 424/499

(58) Field of Classification Search
USPC .......................... 514/57, 54; 536/56; 424/499
See application file for complete search history.

(56) References Cited

U.S. PATENT DOCUMENTS

| | | | |
|---|---|---|---|
| 4,140,760 A | | 2/1979 | Withington |
| 5,972,388 A | * | 10/1999 | Sakon et al. .................. 424/499 |
| 2002/0119104 A1 | | 8/2002 | Rosenthal et al. |
| 2007/0014860 A1 | | 1/2007 | Rosenthal et al. |
| 2007/0202058 A1 | | 8/2007 | Calton |

FOREIGN PATENT DOCUMENTS

| | | |
|---|---|---|
| GB | 2378176 | 2/2003 |
| WO | 9963986 | 12/1999 |
| WO | WO 2007/133082 A1 * | 11/2007 |

OTHER PUBLICATIONS

Simpson (School of Medicine UT Heath Science Center; Feb. 2003, pp. 1-4).*
Batcherior, Hannah. Autmn/Winter 2004 Novel Bioadhesive for Formulations in Drug Delivery. The Drug Delivery Company's Report, PharmaVentures LTD. pp. 16-19.
Batcherior, Hannah. 2005. Scientifically Speaking: Formulation strategies in mucosal-adhesive drug delivery. Controlled Release Society. vol. 22, No. 1, pp. 4-5, 27.
Man Tang, Peter Dettmar, Hannah Batchelor. Mar. 2005. Bioadhesive oesophageal bandages: protection against acid and pepsin injury. International Journal of Pharmaceutics. vol. 292, Issues 1-2, 23 , pp. 169-177.
Non-Final Office Action for U.S. Appl. No. 11/953,030 Office Notification Date of Feb. 4, 2011, App. Filing Date Dec. 8, 2007, Inventor Michael James (28 pages).
International Search Report and Written Opinion for International App. No. PCT/US2008/85859, Date of Mailing Feb. 9, 2009, International Filing Date Dec. 8, 2008, Application Koufman, Jamie (9 pagest).

* cited by examiner

*Primary Examiner* — Shaojia Anna Jiang
*Assistant Examiner* — Michael C Henry
(74) *Attorney, Agent, or Firm* — Ostrolenk Faber LLP

(57) ABSTRACT

A method for treating or preventing disorders, diseases, and symptom of reflux, that is laryngopharyngeal reflux (LPR), in the laryngopharynx caused by pepsin comprises orally administering to the laryngopharynx of a patient an effective amount of cellulose powder. A method for treating or preventing damage to the lining membranes of at least some of the aerodigestive tract, the damage caused by pepsin, comprises coating at least some of the lining membranes with an effective amount of a cellulose powder. Upon inhalation of the powder, the powder coats the lining membranes. Upon coating the lining membranes, the powder becomes a gel. The gel prevents the pepsin from binding with the lining membranes, thereby preventing damage caused by pepsin in laryngopharyngeal reflux or in extra-esophageal reflux.

17 Claims, 2 Drawing Sheets

METHOD FOR PREVENTION AND TREATMENT OF REFLUX INJURY IN THE AERODIGESTIVE TRACT AND LARYNGOPHARYNX CAUSED BY PEPSIN

This application is a continuation of U.S. patent application Ser. No. 11/953,029, filed Dec. 8, 2007, which is hereby incorporated by reference.

BACKGROUND

For the last 50 years, antireflux treatments have been directed at the neutralization or suppression of stomach acid. Antacids (e.g., Mylanta, Gaviscon), H2-antagonists (e.g., Zantac, Pepcid), and proton pump inhibitors (e.g., Prilosec, Nexium) are among the leading-selling drugs in the world.

The term "reflux" means "backflow." The backflow of stomach (gastric) contents into the esophagus is known as gastroesophageal reflux disease (GERD). In the last decade, the backflow of stomach contents into the upper aerodigestive (airway and digestive) tract has become increasingly recognized as an important factor in the development of many common diseases. The medical terms for this are laryngopharyngeal reflux (LPR) and extra-esophageal reflux (EER). Both terms are commonly used; however, EER is the broader of the two terms. The laryngopharynx includes the voice box as well as the pharynx (the upper and lower parts of the throat); however, EER also refers to gastric reflux into any part of the aerodigestive tract, including the uppermost parts of the airway and digestive tracts, e.g., the mouth, oropharynx, nasopharynx, nose, and sinuses.

EER is different in many ways from GERD. What makes EER particularly important and insidious is the fact that it can be "silent," that is, it can occur without any digestive symptoms such as heartburn (reflux-related chest pain). Both EER and GERD are associated with the development of many common aerodigestive tract diseases, including esophagitis, esophageal cancer, pharyngitis, laryngitis, sinusitis, and chronic lung diseases such as asthma.

Scientific studies have shown that gastric juice, referred to as the refluxate, has two ingredients, acid and pepsin. Pepsin is the primary digestive enzyme of the stomach. Contrary to popular belief, it is pepsin, not acid, that produces disease.

When gastric liquid containing acid and pepsin finds its way back up into the throat area (which should not happen but does on occasion) the lining membranes of the throat try to increase protective mucus production. However, this response is usually insufficient to protect against the acid and pepsin.

In the throat and respiratory tract area, active pepsin can bind to the tissue where it can cause many symptoms and even serious tissue damage over a period of time. This can range from a sore throat to cancer and death. Pepsin actually attacks and takes apart the surface of the cells of the lining membranes leaving them exposed to germs. If fact, active pepsin alone can cause the death of otherwise healthy throat lining membranes.

Thus, a need presently exists for a method for prevention and treatment of reflux injury in the laryngopharynx caused by pepsin. A need also exists for an apparatus for orally dispensing a composition, such as a powdered composition, into the aerodigestive tract in general, and specifically into the laryngopharynx.

SUMMARY

A method for treating or preventing disorders, diseases, and symptoms of reflux in the laryngopharynx caused by pepsin comprises administering to the laryngopharynx of a patient an effective amount of cellulose powder. A method for treating or preventing damage to the lining membranes of at least some of the aerodigestive tract, the damage caused by pepsin, comprises coating at least some of the lining membranes with an effective amount of a cellulose powder. The cellulose powder is essentially pure hydroxypropyl methylcellulose powder. The cellulose powder may be delivered orally through inhalation. The powder has an effective particle size such that upon inhalation it is deposited onto the lining membranes of the larngopharynx, or other areas of the aerodigestive tract of the patient.

DETAILED DESCRIPTION

Figure 1:
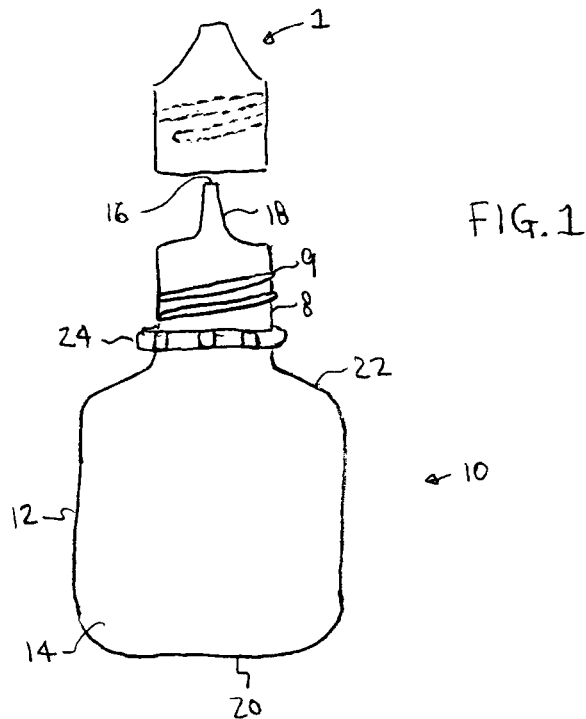
FIG. 1 is a bottle for dispensing a powdered material.

Methylcellulose is sold under a variety of trade names and used in a variety of food products, cosmetic products, and consumer products. It is non-toxic, not digestible, and non-allergenic. It passes through the human body harmlessly.

A method for treating or preventing disorders, diseases, and symptom of reflux, that is laryngopharyngeal reflux (LPR), in the laryngopharynx caused by pepsin comprises orally administering to the laryngopharynx of a patient an effective amount of cellulose powder. Upon inhalation of the powder, the powder coats the lining membranes of the laryngopharynx. Upon coating the lining membranes, the powder becomes a gel. The gel prevents the pepsin from binding with the lining membranes, thereby preventing damage caused by pepsin in laryngopharyngeal reflux. Similarly, a method for treating or preventing damage to the lining membranes of at least some of the aerodigestive tract, the damage caused by pepsin, comprises coating at least some of the lining membranes with an effective amount of a cellulose powder.

In tests, the method was extremely successful in reducing symptoms of LPR. Specifically, symptoms were reduced in over 70% of patients so treated. The cellulose powder was administered orally, but alternatively or additionally be administered intranasally.

As disclosed above, the cellulose powder may be a methylcellulose powder. The cellulose powder may comprise hydroxypropyl methylcellulose powder, or any other equivalent powdered cellulose derivative. The size of the particles comprising the powder is selected such that upon inhalation the particles are effectively and primarily deposited in the laryngopharynx, thus coating the laryngopharynx. Additionally, the particles are sized such that they are neither primarily deposited in the mouth, nor primarily deposited deep into the windpipe. In one example, the particle size is between around 5 micrometers and around 7.5 micrometers. It is appreciated that the effective amount may have a wide range. One example of an effective amount is around 3 milligrams to around 60 milligrams, however other effective amounts are possible.

The method may be carried out when symptoms of LPR or EER present themselves, or as a preventative measure daily or multiple times a day whether or not symptoms are present (as is the case with silent LPR). For example, the method may be carried out one to three times a day, such as upon rising in the morning, prior to significant exposure to substances and foods that exacerbate LPR, and before bed. Adverse affects or overdose from repeated applications of the method is substantially nonexistent. This is the case since the disclosed powdered cellulose is a pharmaceutically inert substance. It is further the case since, as disclosed, the powdered cellulose is substantially pure, such as of a "pharmaceutical grade", that is it does not contain active ingredients such as pharmaceuticals, drugs, or herbs of the prior art, and it is substantially free from impurities.

The cellulose powder may comprise secondary substances. One example of a secondary substance is alginate. The secondary substances may comprise inert substances such as colorants, sweeteners, flavorants, or substances inert to the human body. The secondary substances may comprise active substances such as prior art pharmaceuticals, drugs, or herbs. Those skilled in the art will appreciate that active substances may modify the substantially nonexistent likelihood of adverse affects disclosed above, and may modify the effective amount.

Figure 3:
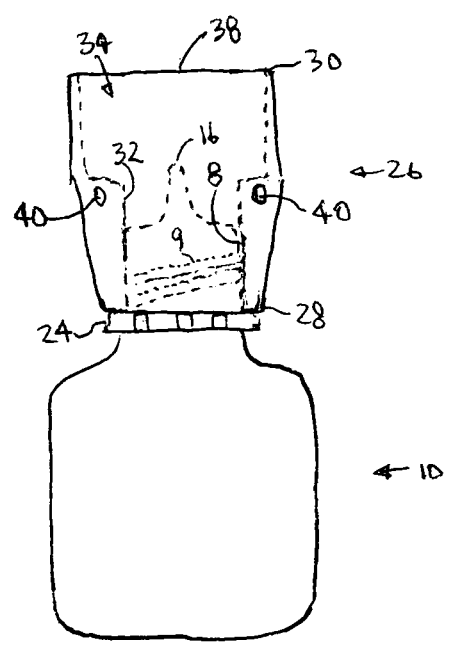
FIG. 3 is an apparatus for dispensing a powdered composition into the aerodigestive tract.

As disclosed above, the powder is orally administered via inhalation. FIG. 3 shows one device for oral administration of the powder via inhalation. It is appreciated that there are various other apparatus that may be effective to administer the powder according to the disclosed method. For example, dry powder inhalation devices such as breath actuated inhalers or passive inhalers may be adapted by those having ordinary skill in the art to administer the powder according to the disclosed method.

FIG. 1 shows a bottle 10 for dispensing a powdered material, and a cap 1. Bottle 10 dispenses powdered material through opening 16. Bottle 10 may further dispense a restricted amount of powdered material such that the amount of powdered material dispensed is regulated. One such bottle is disclosed in U.S. Patent Application Publication No. 2004/0082907 A1, which is hereby incorporated by reference in its entirety.

Briefly, upon pressing the body portion 12 of the bottle 10, a quantity of powdered material in internal cavity 14 is dispensed through opening 16. The bottle is formed from a thermal plastic material such as polyvinylchloride or of any suitable deformable material. An internal cavity 14 of the bottle 10 provides a repository for a quantity of powdered material. The cylindrical bottle 10 comprises a substantially cylindrical body portion 12, extending between a first end portion 20 and shoulder portion 22. However, the bottle may comprise any shape. The first end portion 20 defines a flat closed end base of the bottle 10. The bottle also comprises a neck portion 8, extending from the shoulder portion 22. Opening 16 is disposed at the tip of the nozzle portion 18. A first annular flange 24 extends around the neck portion 8.

Figure 2A:
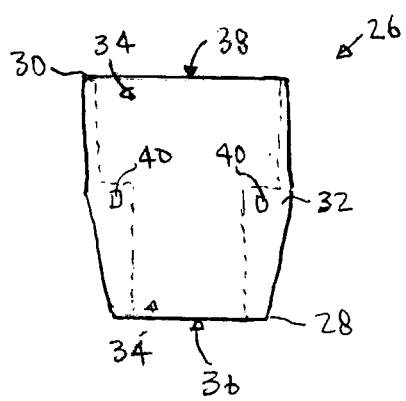
FIG. 2A is a side view of an inhalation attachment for a bottle for dispensing a powdered material into the aerodigestive tract.
Figure 2B:
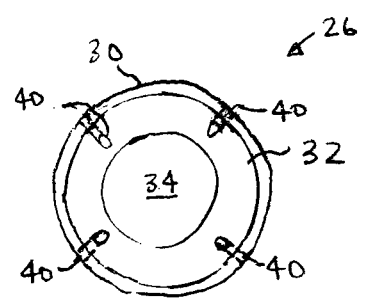
FIG. 2B is a top view of an inhalation attachment for a bottle for dispensing a powdered material into the aerodigestive tract.

FIG. 2A is a side view of an inhalation attachment 26 for a bottle for dispensing a powdered material into the aerodigestive tract. FIG. 2B is the top view of an inhalation attachment 26 for a bottle for dispensing a powdered material into the aerodigestive tract. The inhalation attachment 26 comprises a base 28, a top 30, and side walls 32. The interior of the attachment comprises a channel 34 having an inlet aperture 36 at the base 28 and an outlet aperture 38 at the top 30. The channel 34 has a diverging taper from base 28 to top 30 to increase the dispensing range and dispersion of the air borne powder during inhalation. However, a more narrow channel 34 with no taper or a narrowing taper or outlet aperture is possible. The attachment further comprises a plurality of apertures 40 around the circumference and through the side walls 32.

FIG. 3 is an apparatus for dispensing a powdered composition into the aerodigestive tract. The base 28 of the inhalation attachment 26 is fitted around the neck portion 8 of the bottle 10 and is retained by friction between the neck portion 8 and inner part of the side walls 32 defining channel 34. The inhalation attachment 26 may also be retained by threads 9. The inhalation attachment 26 is attached so that the base 28 meets annular flange 24.

In use, a user depresses inwardly the flexible body portion 12, forcing an amount of powdered composition from the internal cavity 14 of the bottle 10, and through the opening 16. Concurrent with depressing the body portion 12, the user inhales. The powdered composition exiting opening 16 is mixed with air drawn in through apertures 40 when the user inhales. This disperses and accelerates the powdered composition. The air and powdered composition travels through channel 34 and out of outlet aperture 38 and the top 30 (around which the user's lips surround), through the user's mouth and, for example, deposited onto the lining membranes of the user's throat, laryngopharynx, or the like.

While the apparatus of FIG. 3 has been described with an inhalation attachment 26 that is detachable from the bottle 10, it is appreciated that the inhalation attachment 26 and bottle 10 may be made such that they are non-detachable, and form a single piece. It is also appreciated that FIG. 3 may include a cap (not shown but akin to cap 1 of FIG. 1) for covering the top 38.

The foregoing detailed description has discussed only a few of the many forms that this invention can take. It is intended that the foregoing detailed description be understood as an illustration of selected forms that the invention can take and not as a definition of the invention. It is only the following claims, including all equivalents, that are intended to define the scope of this invention.

What is claimed is:

1. A method for ameliorating symptoms of laryngopharyngeal reflux caused by activated pepsin comprising: providing, in an inhalable form and in a form ready for coating lining membranes of laryngopharynx of a patient, an effective amount of dispersible cellulose powder, the effective amount of cellulose powder, upon coating said lining membranes, forming a gel on the lining membranes to prevent pepsin from binding to said lining membranes.

2. The method of claim 1, wherein the cellulose powder is provided to be administered by the patient, and wherein the administering comprises inhaling the effective amount of cellulose powder.

3. The method of claim 1, wherein the cellulose powder comprises a methylcellulose powder.

4. The method of claim 1, wherein the cellulose powder comprises a hydroxypropyl methylcellulose powder.

5. The method of claim 1, wherein the cellulose powder comprises a particle size between about 5 micrometers and around 7.5 micrometers.

6. The method of claim 1, wherein the cellulose powder is free from pharmaceuticals.

7. The method of claim 1, wherein the cellulose powder further comprises another inert substance.

8. The method of claim 1, wherein the cellulose powder is pharmaceutical grade.

9. The method of claim 1, wherein the effective amount is in the range of 3 to 60 milligrams.

10. A method for reducing damage caused by pepsin to lining membranes of laryngopharynx, comprising: providing an inhalant that comprises dispersible and inhalable cellulose powder having a particle size selected to reach the laryngopharynx upon inhalation of the inhalant, the cellulose powder being provided in an effective amount to coat the lining membranes to form a gel that prevents pepsin from binding to the lining membranes coated by the formed gel.

11. The method of claim 10, wherein the cellulose powder comprises a methylcellulose powder.

12. The method of claim 10, wherein the cellulose powder comprises a hydroxypropyl methylcellulose powder.

13. The method of claim 10, wherein the particle size is between 5 micrometers and 7.5 micrometers.

14. The method of claim 10, wherein the inhalant is free from pharmaceuticals.

15. The method of claim 10, wherein the inhalant further comprises another inert substance.

16. The method of claim 10, wherein the inhalant is pharmaceutical grade.

17. The method of claim 10, wherein the effective amount is in the range of 3 to 60 milligrams.

* * * * *